United States Patent [19]
Chow

[11] Patent Number: 5,409,841
[45] Date of Patent: Apr. 25, 1995

[54] ULTRAVIOLET LIGHT STERILIZED SAMPLING DEVICE AND METHOD OF SAMPLING

[76] Inventor: Timothy Chow, P.O. Box 667, Hanover, N.H. 03755

[21] Appl. No.: 669,498

[22] Filed: Mar. 14, 1991

[51] Int. Cl.⁶ .............................................. G01N 1/10
[52] U.S. Cl. .................................. 436/180; 422/24; 422/100; 422/104; 435/292; 73/864.52
[58] Field of Search .................. 422/24, 100, 104; 250/436, 432 R; 137/237; 73/864.31, 864.52; 53/425, 426; 435/292, 294

[56] References Cited

U.S. PATENT DOCUMENTS

| | | | |
|---|---|---|---|
| 2,028,256 | 1/1936 | Stevens et al. | 422/24 X |
| 3,906,236 | 9/1975 | Callahan | 250/455 |
| 3,954,407 | 5/1976 | Andary et al. | 21/83 |
| 4,121,107 | 10/1978 | Bachmann | 250/455 |
| 4,133,863 | 1/1979 | Koenig | 422/99 |
| 4,135,269 | 1/1979 | Marston | 15/4 |
| 4,140,108 | 2/1979 | Nugent | 128/2 F |
| 4,170,798 | 10/1979 | Krumdieck | 73/864.52 X |
| 4,175,140 | 11/1979 | Bachmann et al. | 426/399 |
| 4,342,915 | 8/1982 | Karamian | 250/436 |
| 4,526,045 | 7/1985 | Reekie | 73/864.52 X |
| 4,621,060 | 11/1986 | Redikultsev et al. | 435/292 |
| 4,656,813 | 4/1987 | Baldini et al. | 53/410 |
| 4,675,301 | 6/1987 | Charneski et al. | 422/100 |
| 4,695,551 | 9/1987 | Samhaber et al. | 435/292 |
| 4,698,206 | 10/1987 | Nevin | 422/24 |
| 4,710,634 | 12/1987 | Brooks | 250/455.1 |
| 4,772,795 | 9/1988 | Sakurai et al. | 250/455.1 |
| 4,776,267 | 10/1988 | Harris | 99/451 |
| 4,780,200 | 10/1988 | Bond et al. | 250/432 R |
| 4,806,770 | 2/1989 | Hylton et al. | 250/455.1 |
| 4,819,276 | 4/1989 | Stevens | 4/233 |
| 4,877,964 | 10/1989 | Tanaka et al. | 250/455.1 |
| 4,888,487 | 12/1989 | Ritter | 250/455.1 |
| 4,896,042 | 1/1990 | Humphreys | 250/435 |
| 4,906,851 | 3/1990 | Beasley et al. | 250/455.1 |
| 4,907,316 | 3/1990 | Kurz | 15/319 |
| 4,942,770 | 7/1990 | Seifert et al. | 73/864.34 |
| 4,952,369 | 8/1990 | Belilos | 422/24 |

OTHER PUBLICATIONS

Nicholas, A. F. 1987. A sterile connection device for cell culture and fermentation systems. Amer. Biotech. Lab. Jul./Aug. 1987.

Webb, C., J. F. Dean, and R. D. Marshall. 1990. Automatic aseptic sampling of fermentaion broth. Bio/Technology 8:926–928.

Charton, R. 1990. Simplifying Sterile access in bioreactor operation. American Biotechnology Laboratory 8:16.

Ghoul, M., E. Ronat, and J. M. Engasser. 1986. An automatic and sterilizable sampler for laboratory fermentors. Biotech/Bioeng 28:119–121.

Fisher Scientific, products catalogue, pp. 1506–1507 (1988).

Block, S. S. "Disinfection, Sterilization, and Preservation", 3rd ed. Philadelphia, Lea & Febiger, 1983, pp. 109–110.

*Primary Examiner*—Jeffrey R. Snay
*Attorney, Agent, or Firm*—Davis, Bujold & Streck

[57] ABSTRACT

An apparatus to take aseptic samples from bioreactors or other aseptic or sterile containers is disclosed. The invention comprises a hollow cannula (20), a septum (28) which seals a pre-sterilized sample tube (27) and an ultraviolet lamp (22). The cannula is connected to a bioreactor which is to be sampled. The ultraviolet lamp is used to produce light which will sterilize the surface of the septum and cannula prior to sampling, thus maintaining asepsis of both the bioreactor and the sample.

10 Claims, 2 Drawing Sheets

ULTRAVIOLET LIGHT STERILIZED SAMPLING DEVICE AND METHOD OF SAMPLING

BACKGROUND—FIELD OF INVENTION

This invention relates to the art of sterile accessing aseptic or sterile processes, specifically to the use of ultraviolet light to sterilize and maintain the sterility of the surface of a sampling device prior to sampling a bioreactor.

BACKGROUND—DESCRIPTION OF PRIOR ART

Bioreactors and fermentors, herein referred to as bioreactors, are used to manufacture chemicals including enzymes, pharmaceutical, food stuff, and pigments, by culturing microorganisms or cells, herein referred to as organisms. Since the environment within the bioreactor is favorable to the growth of many undesirable microorganisms normally present in the environment, bioreactors must exclude all undesirable microorganisms. However, in order to monitor the manufacturing process within the bioreactor it is desirable to take samples from the bioreactor. Sampling should be done in a such a fashion as to reduce the risk of introducing undesirable microorganisms into the bioreactor. Furthermore it is often desirable for the resulting sample to be free from contamination by undesirable microorganisms.

The normal state of bioreactors is aseptic, meaning they contain only the desired organism and are free from undesirable organisms. Sterility is defined as the absence of all organisms. All devices used for aseptic sampling are also capable of sterile sampling, therefore herein aseptic sampling will refer to both aseptic and sterile sampling.

Several methods are known to minimize risk of contamination during aseptic sampling of bioreactors. "Sampling bells" are often incorporated into bioreactors. These devices consist of an opening to the bioreactor which is protected from undesirable microorganisms by a hood which inhibits air circulation around the opening. The opening of the hood is directed downward so that microorganisms which settle due to gravity will not contact the opening. Sampling is accomplished by expelling liquid from the reactor into a sample vessel through the opening. "Sampling bells" are not completely effective at preventing airborne microorganisms from reaching the opening to the bioreactor. They also do not kill microorganisms around the opening.

Steam is also known to be used to sterilize the connections between the interior of the bioreactor and aseptic sampling vessel. Steam, however is corrosive to many materials used to construct such an apparatus, is dangerous to operators, and is often not readily available. Furthermore sufficient time must be allowed for complete sterilization, usually 15 minutes at 15 psig of steam pressure, and for the connection to cool. Since the connections must withstand pressure the use of steam is prohibitive to the automation of the sampling process.

"Flaming" is also known to be used to aseptically sample bioreactors. In "flaming" a flame is used to heat sterilize the surface of a tube or connector which communicates through a valve to the interior of the bioreactor prior to sampling. Flaming is an unreliable means of sterilization and the process is difficult to automate. However, Webb et al. (1990) described an automated sampler where multiple sample tubes are connected by flaming and samples are then taken at preset time intervals.

Laminar flow hoods are also known to be used to make sterile connections. Laminar flow hoods inhibit contamination by microorganisms by passing a flow of sterile air over exposed connections which have previously been sterilized by other means. The flow of sterile air prevents contaminated air from the environment from reaching the exposed connections. Additionally ultraviolet lights may be used to sterilize the surfaces of the hood when not in use. Laminar flow hoods are expensive and bulky, and do not kill microorganisms which may be present on the surface of the apparatus. Making reliable sterile connections within a laminar flow hood require a highly skilled person trained in aseptic technique.

Plastic welding is also known to be used to make aseptic connections to bioreactors. Du Pont Company manufactures a portable tubing welder called a STERILE CONNECTION DEVICE (TM), SCD IIB described by Charton (1990) and Nicholas (1987). With the device two pieces of sterile thermoplastic tube can be welded together without contamination. This device has not gain wide spread use because of the high initial cost. This method of sampling is also difficult to automate.

Filters and semipermeable membranes are also known to be used to aseptically sample bioreactors (U.S. Pat. No. 4,695,551). This method does not allow for sampling of the organisms within the bioreactor and the filter or semipermeable membrane may bias the sample taken. Undesirable organisms on the non-sterile side of filters can "grow through" to the sterile side if the filter is wet, and they are given enough time. Wet filters are generally not considered a good sterile barrier over long periods of time. Ghoul et al. (1986) shows an automated devices using semipermeable membranes.

U.S. Pat. No. 4,942,770 describes an automatic aseptic sampling apparatus which uses air breaks and check valves to maintain asepsis. Since contaminating organisms are present in air, and since check valve seals are not normally considered to be good aseptic seals, this method has not gained wide spread use.

Septum ports are also known to be used to aseptically sample bioreators. Septum ports are elastomeric material separating the non-sterile environment from the aseptic bioreactor, which can be pierced by a sterile cannula through which an aseptic sample can be drawn. The septa are sterilized by rinsing with alcohol and/or by flaming prior to piercing with the cannula. However, sterilization is often incomplete, microorganisms in the air will often re-contaminate the surface of the septa or cannula prior to piercing with the cannula, and the septa after repeated sampling will often leak and provide a path for undesirable organisms to contaminate the bioreactor.

The germicidal effects of ultraviolet light are very well known. Ultraviolet light has been used to sterilize solid surfaces (U.S. Pat. Nos. 4,952,369, 4,896,042, 4,877,964) as well as fluids. The germicidal effects of ultraviolet light have been used sterilize toothbrushes (U.S. Pat. Nos. 4,906,851, 3,954,407, 4,888,487, 4,806,770), mops (U.S. Pat. No. 4,135,269), door handles (U.S. Pat. No. 4,710,634), toilet seats (U.S. Pat. No. 4,819,276), foodstuff and associated packaging (U.S.

Pat. Nos. 4,175,140, 4,121,107, 4,776,267), drinking glasses (U.S. Pat. No. 3906236), floor coverings(U.S. Pat. No. 4,907,316), dental tools (U.S. Pat. Nos. 4,698,206, 4,772,795) and plastic bags (U.S. Pat. No. 4,656,813). These teachings, however, do not pertain to the sampling of bioreactors.

The use of evacuated or partially evacuated tubes to draw physiological fluid samples is known (U.S. Pat. Nos. 4,140,108, 4,133,863). These teachings, however, do not pertain to the aseptic or sterile sampling of bioreactors, or to automatic sampling. These teachings also do not show the sterilization of the external surfaces with ultraviolet light before sampling.

SUMMARY OF THE INVENTION

A primary objective of the present invention is to provide a device to take sterile or aseptic samples from a sterile or aseptic vessel while maintaining asepsis or sterility of both the samples and the vessel and which does not exhibit the aforesaid drawbacks and shortcomings of the prior art construction.

A further object of the present invention is to provide a device which will take such samples automatically at predetermined intervals without operator intervention.

A further object of the present invention is to allow continuous series of samples to be introduced to non-sterile analytic instruments for example, high performance liquid chromatographs (HPLC), capillary electrophoresis, and glucose analyzers, in an automated fashion. Thus allowing continuous automated monitoring of aseptic processes.

Now in order to implement these and still further objects of the invention, which will become more readily apparent as the description proceeds, the present invention comprises a hollow cannula, a septum which seals a sterile sample tube and an ultraviolet lamp. The cannula is connected to an aseptic vessel which is to be sampled. The ultraviolet lamp is used to produce light which will sterilize the surface of the septum and cannula prior to sampling, thus maintaining asepsis of both the vessel and the sample.

REFERENCE NUMERALS IN DRAWINGS

20 Cannula
21 UV Chamber
22 UV Lamp
23 Clear plastic Box—Assembled
23A Clear plastic Box—Front
23B Clear plastic Box—Right Side
23C Clear plastic Box—Left Side
23D Clear plastic Box—Back
23E Clear plastic Box—Base
24 Tube Shuttle—Assembled
24A Tube Lock
24B Tube Shuttle—Lower Structure
24C Tube Shuttle—Slides
25 Bioreactor
26 Pinch Clamp
27 Sterile Sample Tube
28 Septum
29 Chamber Door
30 UV Lamp Power Supply
31 Tube Shuttle Handle
32 Silicone Tube
33 Reflective Surface

DESCRIPTION OF PREFERRED EMBODIMENT

Figure 1:
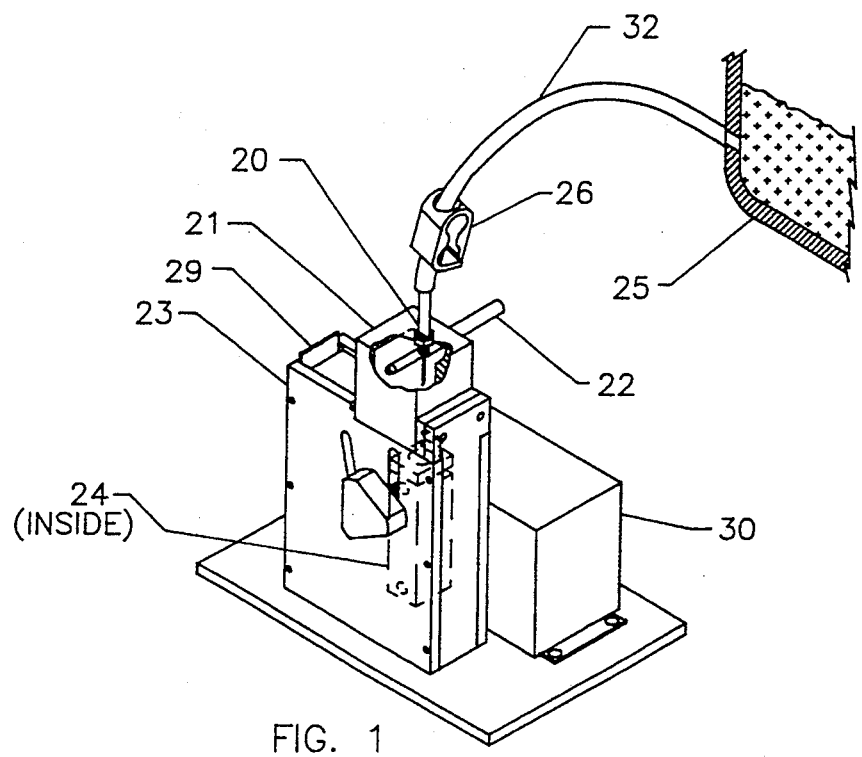
FIG. 1 is perspective of the preferred embodiment of the invention showing the left rear of the device, with part of the UV chamber 21, removed to show the UV lamp 22 and cannula 20.
Figure 2:
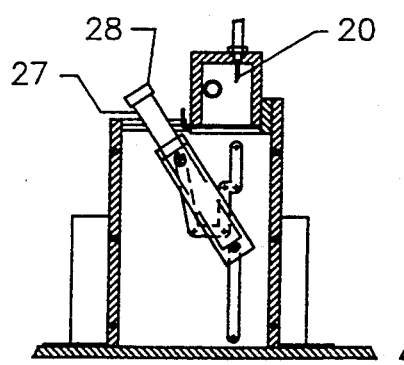
FIG. 2 is a plan view of the right side of the preferred embodiment with the shuttle handle 31 and right side 23B removed for clarity. The tube shuttle 24 is in the load position and the chamber door 29 is in the aft position.
Figure 3:
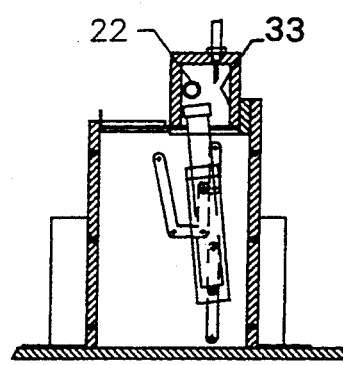
FIG. 3 is a plan view of the right side of the preferred embodiment with the shuttle handle 31 and right side 23B removed for clarity. The tube shuttle 24 in the sterilize position and the chamber door 29 in the forward position.
Figure 4:
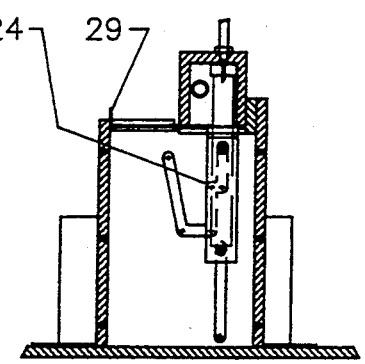
FIG. 4 is a plan view of the right side of the preferred embodiment with the shuttle handle 31 and right side 23B removed for clarity. The tube shuttle 24 in the sample position and the chamber door 29 in the forward position.
Figure 5:
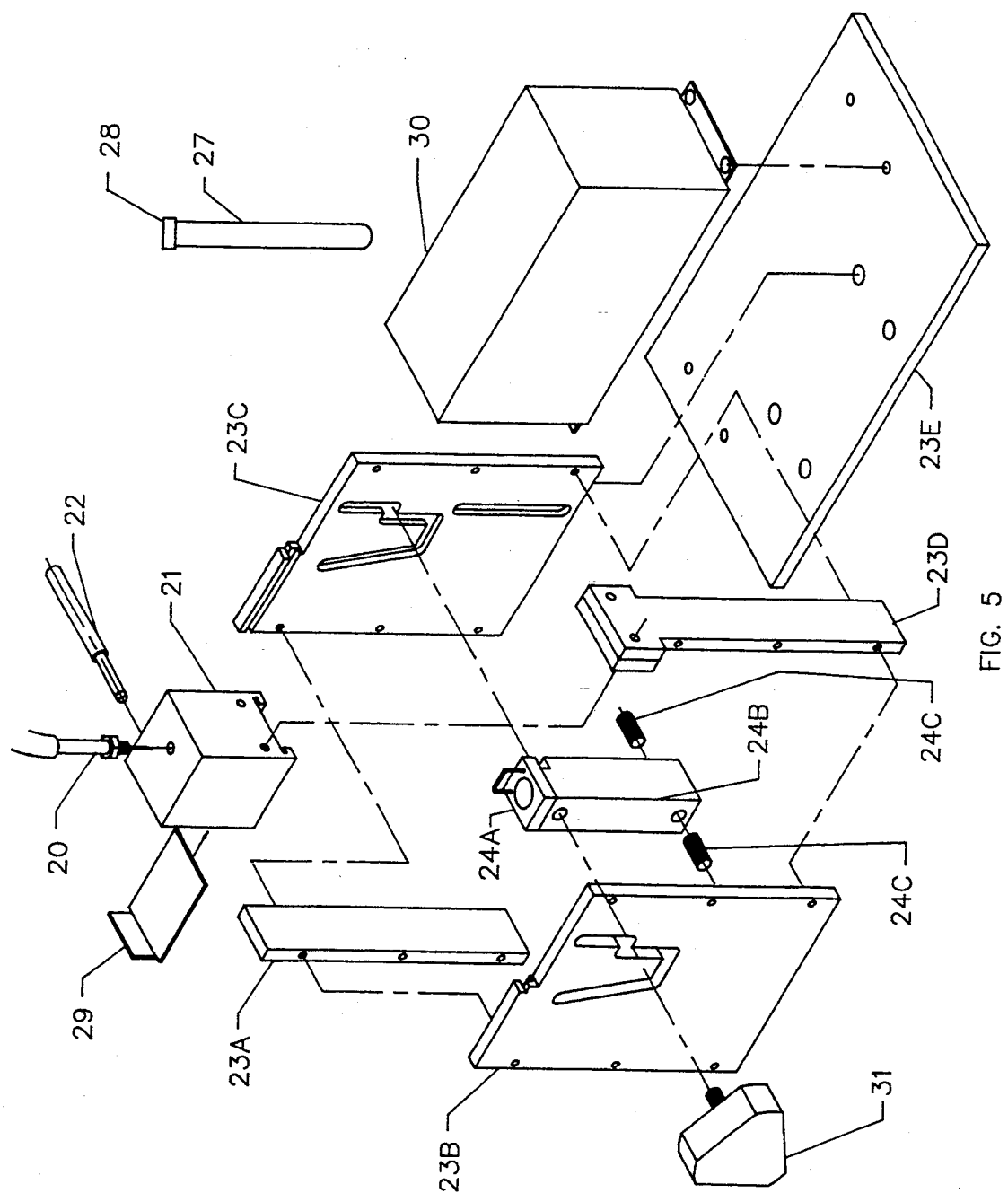
FIG. 5 shows an exploded perspective view of the preferred embodiment.

Referring to FIG. 1. and FIG. 5, the preferred embodiment of this invention consists of a hollow cannula 20 that is mounted into the UV chamber 21 which forms a hood over the cannula 20 and also supports an ultraviolet (UV) lamp 22. The UV chamber 21 is mounted on a clear plastic box 23 with slots to guide the robe shuttle 24 into three positions. The load position is seen in FIG. 2., the sterilize position in FIG. 3., and the sample position in FIG. 4. The cannula 20 communicates to the bioreactor 25 from which samples are to be drawn via a silicone tube 32 and a pinch valve 26.

The UV chamber 21 protects the cannula 20 from air currents which might otherwise carry microorganisms to the cannula surface, and from microorganisms which might otherwise settle due to gravity on the cannula surface. The UV chamber also houses the UV lamp 22 and has a curved reflective surface 33 which focuses the ultraviolet light onto the cannula surfaces which are not directly exposed to the light. The ultraviolet light emitted from the lamp will kill microorganisms within the UV chamber by direct exposure. Additionally microorganisms will be killed by the ozone produced from the oxygen in air if a short wave length (under 200 nm) ultraviolet lamp is used. Additionally microorganisms can further be excluded from within the UV chamber 21 by blowing sterile filtered air through the interior of the UV chamber (not shown).

In the preferred embodiment of the invention, sample tubes 27 are closed tubes which have been evacuated and sterilized prior to use. They are sealed by means of a rubber septum 28 which maintains the vacuum and sterility but can be penetrated by the cannula 20.

The sample tube 27 and septum 28 are loaded into the tube shuttle support mechanism 24 while the chamber door 29 is in the aft position, FIG. 2. In this position the chamber door 29 seals the UV chamber 21 from airborne contaminants carried by air convection. The tube shuttle 24 is lowered and the chamber door 29 is moved forward, FIG. 3. In this position the chamber door 29 still prevents air currents from entering the UV chamber 21 by blocking the entrance to the plastic box 23.

The sample tube 27 and septum 28 are then positioned so that the septum surface is within the UV chamber 21 and directly below the ultraviolet lamp 22, FIG. 4. The tube is held in this position until enough time has elapsed for the light to have sterilized the surface of the septum.

The tube shuttle 24 is then slid up, allowing the cannula 20 to pierce the septum 28, FIG 4. The pinch valve 26 is then opened, and since the sample tube 27 is evacuated liquid will be drawn from tile bioreactor 25 into tile sample tube 27. When the tube is full the vacuum will be gone and the flow of liquid will stop, therefore there is no chance of over-filling the sample tube. The pinch valve 26 is then closed and the sample tube 27 is removed.

In another embodiment of the invention (not shown) a plurality of sample tubes can be used and the movement of the sample tubes, pinch valve and cannula can be automated so that samples can be taken at predetermined time intervals without the need for operator intervention.

While the presently depicted devices have been described in connection with the sampling of bioreactors, it can be readily envisioned how sterile or aseptic fluid can be introduced or extracted from other sterile or aseptic vessels. Accordingly, it is intended that the scope of this patent be limited only by the appended claims:

What I claim is:

1. A sampling apparatus for supplying one of an aseptic and sterile fluid sample from a corresponding one of an aseptic and sterile vessel, said apparatus comprising:
   (a) a main housing;
   (b) a sample receptacle shuttle support mechanism being located within said main housing and supporting a sample receptacle having a cannula-penetrable septum and a sterile interior;
   (c) an ultraviolet irradiating housing having an opening communicating with said main housing;
   (d) a cannula having a sterile interior and defining a longitudinal axis, said cannula being located within said ultraviolet irradiating housing, a first end of said cannula communicating with a vessel to facilitate transportation of a fluid sample, via said cannula, from the vessel to said sample receptacle carried by said sample receptacle shuttle support mechanism;
   (e) an ultraviolet light source being located within said ultraviolet irradiating housing, said ultraviolet light source being positioned so as to facilitate simultaneous sterilization of said cannula and the cannula-penetrable septum of said sample receptacle, prior to engagement between the septum and said cannula, when said sample receptacle is positioned by said sample receptacle shuttle support mechanism proximate said opening; and
   (f) a conveying mechanism for moving said sample receptacle relative to said cannula from a first position, in which said sample receptacle is located proximate said opening to facilitate simultaneous sterilization of both said cannula and the cannula-penetrable septum of said sample receptacle, to a second position, in which a second end of said cannula pierces the cannula-penetrable septum and communicates with an interior of said sample receptacle to facilitate transportation of the fluid sample from the vessel to the interior of said sample receptacle, and for returning said sample receptacle back to the first position.

2. The apparatus according to claim 1 wherein said ultraviolet irradiating housing has an interior reflective surface which, during activation of said ultraviolet light source, reflects ultraviolet light emitted from said ultraviolet light source back toward said cannula and the cannula-penetrable septum.

3. The apparatus according to claim 1 wherein a sterile elongate transport tube facilitates communication between the first end of said cannula and the vessel and a valve is provided at a desired location along said elongate transport tube for controlling fluid sample flow from the vessel to said cannula.

4. The apparatus according to claim 1 wherein said main housing is larger in size than said ultraviolet irradiating housing.

5. The apparatus according to claim 1 wherein said sample receptacle is at least partially evacuated to assist with transfer of the fluid from the vessel to a said sample receptacle.

6. The apparatus according to claim 1 wherein, during use, said ultraviolet irradiating housing is vertically positioned above said main housing so that said cannula is protected from unsterile matter settling on said cannula due to gravity.

7. The apparatus according to claim 6 wherein said opening is of a size to allow the cannula-penetrable septum to pass therethrough while minimizing contamination of said ultraviolet irradiating housing by air borne contaminants.

8. The apparatus according to claim 7 wherein said conveying mechanism further comprises a mechanism for positioning said sample receptacle shuttle support mechanism at a location for one of attaching and removing a said sample receptacle from said sample receptacle shuttle support mechanism.

9. The apparatus according to claim 8 wherein said opening includes a door and a door control mechanism for closing said door, when one of attaching and removing said sample receptacle from said sample receptacle shuttle support mechanism is desired, and for opening said door when said sample receptacle is moved proximate said opening.

10. A method of acquiring one of an aseptic and sterile fluid sample from a corresponding one of an aseptic and sterile vessel with a sampling apparatus for supplying one of an aseptic and sterile fluid sample from a corresponding one of an aseptic and sterile vessel, said apparatus comprising a main housing; a sample receptacle shuttle support mechanism being located within said main housing and supporting a sample receptacle having a cannula-penetrable septum and a sterile interior; an ultraviolet irradiating housing having an opening communicating with said main housing; a cannula having a sterile interior and defining a longitudinal axis, said cannula being located within said ultraviolet irradiating housing, a first end of said cannula communicating with a vessel to facilitate transportation of a fluid sample, via said cannula, from the vessel to said sample receptacle carried by said sample receptacle shuttle support mechanism; an ultraviolet light source being located within said ultraviolet irradiating housing, said ultraviolet light source being positioned so as to facilitate simultaneous sterilization of said cannula and the cannula-penetrable septum of said sample receptacle, prior to engagement between the septum and said cannula, when said sample receptacle is positioned by said sample receptacle shuttle support mechanism proximate said opening; and a conveying mechanism for moving said sample receptacle relative to said cannula from a first position, in which said sample receptacle is located proximate said opening to facilitate simultaneous sterilization of both said cannula and the cannula-penetrable septum of said sample receptacle, to a second position, in which a second end of said cannula pierces the cannula-penetrable septum and communicates with an interior of said sample receptacle to facilitate transportation of the fluid sample from the vessel to the interior of said sample receptacle, and for returning said sample receptacle back to the first position; said method comprising the steps of:

(a) placing a sample receptacle in said sample receptacle shuttle support mechanism;

(b) locating said sample receptacle proximate said opening via said sample receptacle shuttle support mechanism;

(c) irradiating both the cannula-penetrable septum of said sample receptacle and said cannula with said ultraviolet light source;

(d) thereafter moving said sample receptacle with said shuttle support mechanism relative to said cannula to pierce the cannula-penetrable septum of said sample receptacle with said cannula;

(e) supplying the fluid sample from the vessel to said sample receptacle; and (f) removing said sample receptacle from said shuttle support mechanism.

* * * * *